United States Patent [19]
Boden et al.

[11] Patent Number: 5,665,697
[45] Date of Patent: Sep. 9, 1997

[54] USE OF 1 (3H)-ISOBENZOFURANONE IN PERFUMERY

[75] Inventors: Richard M. Boden, Ocean; William L. Schreiber, Freehold, both of N.J.

[73] Assignee: International Flavors & Fragrances Inc., New York, N.Y.

[21] Appl. No.: 733,388

[22] Filed: Oct. 18, 1996

Related U.S. Application Data

[60] Provisional application No. 60/006,159, Nov. 2, 1995.

[51] Int. Cl.[6] ............................................. A61K 7/46
[52] U.S. Cl. ............................................. 512/13
[58] Field of Search ........................... 512/13; 514/470

[56] References Cited

U.S. PATENT DOCUMENTS

| | | | |
|---|---|---|---|
| 4,082,716 | 4/1978 | Fielding et al. | 260/30.4 R |
| 4,233,161 | 11/1980 | Sato et al. | 252/1 |

FOREIGN PATENT DOCUMENTS

| | | | |
|---|---|---|---|
| 707575 | 4/1996 | European Pat. Off. | |
| 8188528 | 7/1996 | Japan | A61K 7/48 |
| 9530667 | 11/1995 | WIPO | C07D 307/83 |

OTHER PUBLICATIONS

Beilstein, p. 161, vol. XVII, No. 310–311, System No. 2463, "Phthalid", Item No. 3 (appearing on pp. 161 and 162).
Mowry, et al, vol. 71, Journal of the American Chemical Society, pp. 120–122, Title: "Vinyl Aromatic Compounds. VI. Alkylidenephthalides and Related Compounds".
Beilstein, vol. E, III/IV 17, System No. 2463/H 310–312, pp. 4948 and 4949.
*Aldrich* Chemical Company Catalog, published 1994 by Aldrich Chemical Company, Inc. of 1001 West Saint Paul Avenue, Milwaukee, Wisconsin 53233, p. 1143 and front cover of catalog, Item No. P3,960-5.

*Primary Examiner*—Raymond Henley, III
*Attorney, Agent, or Firm*—Arthur L. Liberman

[57] ABSTRACT

Described is the use of 1(3H)-isobenzofuranone having the structure:

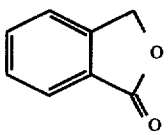

in augmenting, enhancing or imparting aromas in or to perfume compositions, colognes and perfumed articles.

2 Claims, 1 Drawing Sheet

USE OF 1 (3H)-ISOBENZOFURANONE IN PERFUMERY

RELATED COPENDING PATENT APPLICATIONS

This Application is a continuation-in-part of provisional specification No. 60/006,159 filed on Nov. 2, 1995, entitled: "USE OF 1(3H)-ISOBENZOFURANONE IN PERFUMERY". Benefit of said specification No. 60/006,159 is hereby claimed under 35 U.S.C. §119(e).

BACKGROUND OF THE INVENTION

This invention covers the use of 1(3H)-isobenzofuranone defined according to the structure:

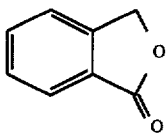

in augmenting, enhancing or imparting aromas in or to perfume compositions, colognes or perfumed articles.

The compound having the structure:

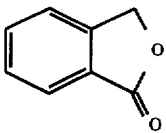

is a known compound. However, its use in perfumery is unknown. Benzofuranone type derivatives, e.g., coumarin, defined according to the structure:

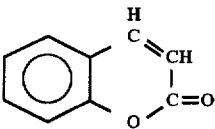

and dihydrocoumarin having the structure:

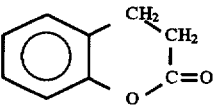

are known in perfumery and their perfumery properties are described by Arctander, "*Perfume and Flavor Chemicals* (Aroma Chemicals)", Volume I, published by the author in 1969 at monographs 704 and 934. Furthermore, diethyl phthalate having the structure:

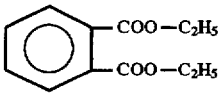

is also known for its use in perfumery as shown by Arctander at monograph 913.

Sweet coumarin-like aromas with almond-like, sweet, hay and heleotropin-like topnotes are highly desirable in the field of perfumery. The prior art does not disclose, expressly or implicitly, the use of the compound having the structure:

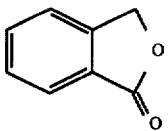

or the creation of the combination of perfumery notes which are not only substantive but powerful as well.

The compound having the structure:

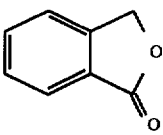

is known as "Phthalide" and is distributed by the Sigma Aldrich Company of 1001 West Saint Paul Avenue, Milwaukee, Wis. 53233. It is listed in the Sigma Aldrich catalog as No. P3960-5 and indicated to have a melting point of 72°–74° C. and a boiling point of 290° C. The synthesis of phthalide is set forth by Chaikin and Brown, "Reduction of Aldehydes, Ketones and Acid Chlorides by Sodium Borohydride" in Volume 71, *J. Am. Chem. Soc.*, January 1949 at pages 122–125.

The syntheses and properties of phthalide having the structure:

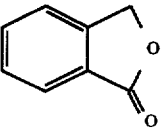

are also set forth in Beilstein [System No. 2463] XVII, 310–311 at pages 161 and 162 and at Beilstein [System No. 4948] E III/IV 17 (ES10).

Isomeric homologs of pthalide are known for use in perfumery, having the structure:

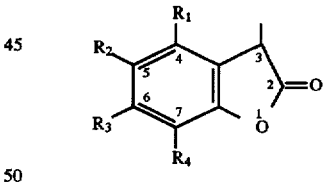

Thus, the genus defined according to the structure is disclosed in European Published Application No. 707,575 as well as PCT Application No. 95/30667, abstracted by DERWENT CHEMICAL PATENTS INDEX ALERTING ABSTRACTS BULLETIN, issued Jun. 14, 1996 as follows: FIRM E1396-010568/01=EP 707575A1 Use of dihydrobenzofuranone derivs. as perfuming ingredients—specific claimed cpds., prepn. and compsns. (Frn)

FIRMENICH SA 94.05.09 94CH-001441

D23 P34 (D21 D25) (96.04.24) *WO 9530667-A1 C07D 307/83,

A61K 7/32, C07D 307/92, A61L 9/01

95.03.27 95EP-911475 95.03.27 95WO-IB00206 Based on WO9530667-A (Eng) R(CH DE FR GB LI NL)

A dihydrobenzofuranone cpd. of formula (I) is used as a perfuming ingredient, $R_1$–$R_4$=H, 1–5C (un)satd. alkyl, 1–4C alkoxy, 5-6C cycloaliphatic or aromatic gp., with the cyclic gp. opt. substd. with 1 or more lower alkyl; or 2 adjacent R gps. together form a 5-6C (un)satd. ring, opt. substd. by 1 or more lower alkyl; and the other 2 gps.=H.

Use—Perfumed articles include toilet waters, soaps, bath or shower gels, shampoos or other hair prods., cosmetics, deodorants for the body or the air, detergents, textile softeners, and prods. for upkeep. Use of 10 cpds. is claimed, esp. 3,4,6-tirmethyl-2H-benzo(b)furan-2-one, 3,6,7-trimethyl-3H-benzo(b)furan-2-one, 3,5,6,7-tetrahydro-3-methyl-indeno(5,6-b)furan-2-one 5,7-diisopropyl-3-methyl-3H-benzo(b)furan-2-one (II) or 5,7-di-tert.-butyl-3-methyl-3H-benzo(b)furan-2-one or a mixt. of (II) and 3-methyl-cyclopentadec-5-en-1-one.

ADVANTAGE—The cpds. impart a lactone, coumarin, fruity or musky note. (Dwg.No.0/0)

CT: 3.Jnl.Ref EP041122 U.S. Pat. No. 4,252,817 WO9412143

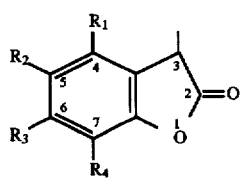

(I)

Thus, in the structure:

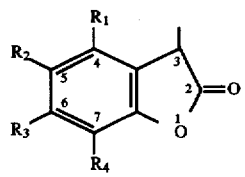

$R_1$, $R_2$, $R_3$ and $R_4$ represent hydrogen or $C_1$-$C_5$ saturated or unsaturated alkyl, $C_1$-$C_4$ alkoxy, $C_5$-$C_6$ cycloaliphatic, or aromatic with the cyclic group optionally substituted with one or more lower alkyl; or two adjacent R groups together form a $C_5$-$C_6$ saturated or unsaturated ring optionally substituted by one or more lower alkyl groups with the other two groups being hydrogen.

However, the genus of compounds having the structure:

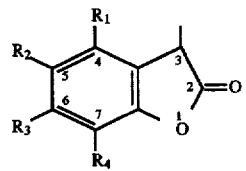

is different in kind rather than degree from the structure of pthalide, to wit:

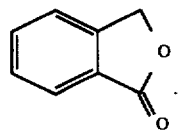

Nothing in the prior art discloses or implies that the compound having the structure:

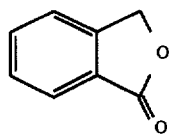

is useful in the field of perfumery. The compound having the structure:

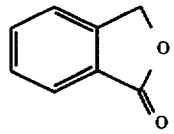

has unobvious, unexpected and advantageous properties over any compounds having related structures existing in the prior art.

THE INVENTION

The instant invention covers the use of the compound having the structure:

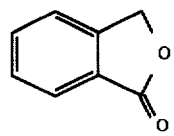

in augmenting, enhancing or imparting aromas in or to perfume compositions or perfumed articles such as solid or liquid anionic, cationic, nonionic or zwitterionic detergents, fabric softener compositions, fabric softener articles, hair preparations, after-shave lotions, perfumed polymers and the like.

The 1(3H)-isobenzofuranone having the structure:

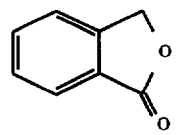

imparts, augments or enhances sweet coumarin-like aromas with almond-like, sweet, hay and heliotropin-like topnotes.

As olfactory agents, the 1(3H)-isobenzofuranone of our invention can be formulated into or used as components of a "perfume composition" or can be used as a component of a "perfumed article" or the perfume composition may be added to perfumed articles.

The term "perfume composition" is used herein to mean a mixture of organic compounds including, for example, alcohols, aldehydes, ketones, nitriles, lactones (other than the lactone of our invention), natural essential oils, synthetic essential oils, and frequently, hydrocarbons which are admixed so that the combined odors of the individual components produce a pleasant and desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh smelling materials.

In perfume compositions, the individual component will contribute its particular olfactory characteristics, but the olfactory effect of the perfume composition will be the sum of the effects of each of the perfume ingredients. Thus, the 1(3H)-isobenzofuranone of our invention can be used to alter the aroma characteristics of a perfume composition, for example, by highlighting or moderating the olfactory reaction contributed by another ingredient in the composition.

The amount of the 1(3H)-isobenzofuranone of this invention which will be effective in perfume compositions, depends on many factors including the other ingredients, their amounts and the effects which are desired. It has been found that perfume compositions containing as little as 1.0% of the 1(3H)-isobenzofuranone of our invention can be used to impart interesting, intense and substantive sweet, coumarinic-like aromas with sweet, hay, heliotropin-like and almond-like topnotes to soaps, liquid and solid, anionic, cationic, nonionic and zwitterionic detergents, cosmetic powders, liquid and solid fabric softeners, optical brightener compositions, perfumed polymers and other products. The amount employed can range up to 50% or higher and will depend on considerations of cost, nature of the end product and the effect desired on the finished product and the particular fragrance sought.

The 1(3H)-isobenzofuranone of this invention can be used alone or taken together with other perfumery components in perfume compositions as an olfactory component in detergents and soaps, space odorants and deodorants; colognes, toilet waters, bath salts, hair preparations, such as lacquers, brilliantines, pomades and shampoos; cosmetic preparations such as creams, deodorants, hand lotions and sun screens; powders such as talcs, dusting powders, face powders and the like. When used as an olfactory component of a perfumed article, as little as 0.01% of the 1(3H)-isobenzofuranone of our invention will suffice to impart interesting, long-lasting, substantive sweet, coumarinic-like aromas with sweet, hay, heliotropin-like and almond-like topnotes. Generally, no more than 0.5% is required.

In addition, the perfume composition can contain a vehicle or carrier for the 1(3H)-isobenzofuranone taken alone or taken together with other ingredients. The vehicle can be a liquid such as an alcohol such as ethanol; a non-toxic glycol such as propylene glycol or the like. The carrier can be an absorbent solid such as a gum (e.g., gum arabic, guar gum and xanthan gum) or components for encapsulating the composition such as gelatin which can used to form a capsule wall surrounding the perfume oil as by means of coacervation.

Our invention also covers the utilization of controlled release technology for the controlled release of perfumes into gaseous environments; odor maskants and deodorizing agents into gaseous environments from polymers, for example, polymers of polyepsilon caprolactone described at column 85 of U.S. Pat. No. 4,956,481, the specification for which is incorporated by reference herein.

Furthermore, the method of incorporating the 1(3H)-isobenzofuranone of our invention for perfume compositions containing same into polymers may be according to the technique of U.S. Pat. No. 3,505,432 issued on Apr. 7, 1970, the specification for which is incorporated by reference herein; or U.S. Pat. No. 4,247,498 issued on Jan. 27, 1981, the specification for which is incorporated by reference herein.

DETAILED DESCRIPTION OF THE DRAWINGS

Figures 1, 2:
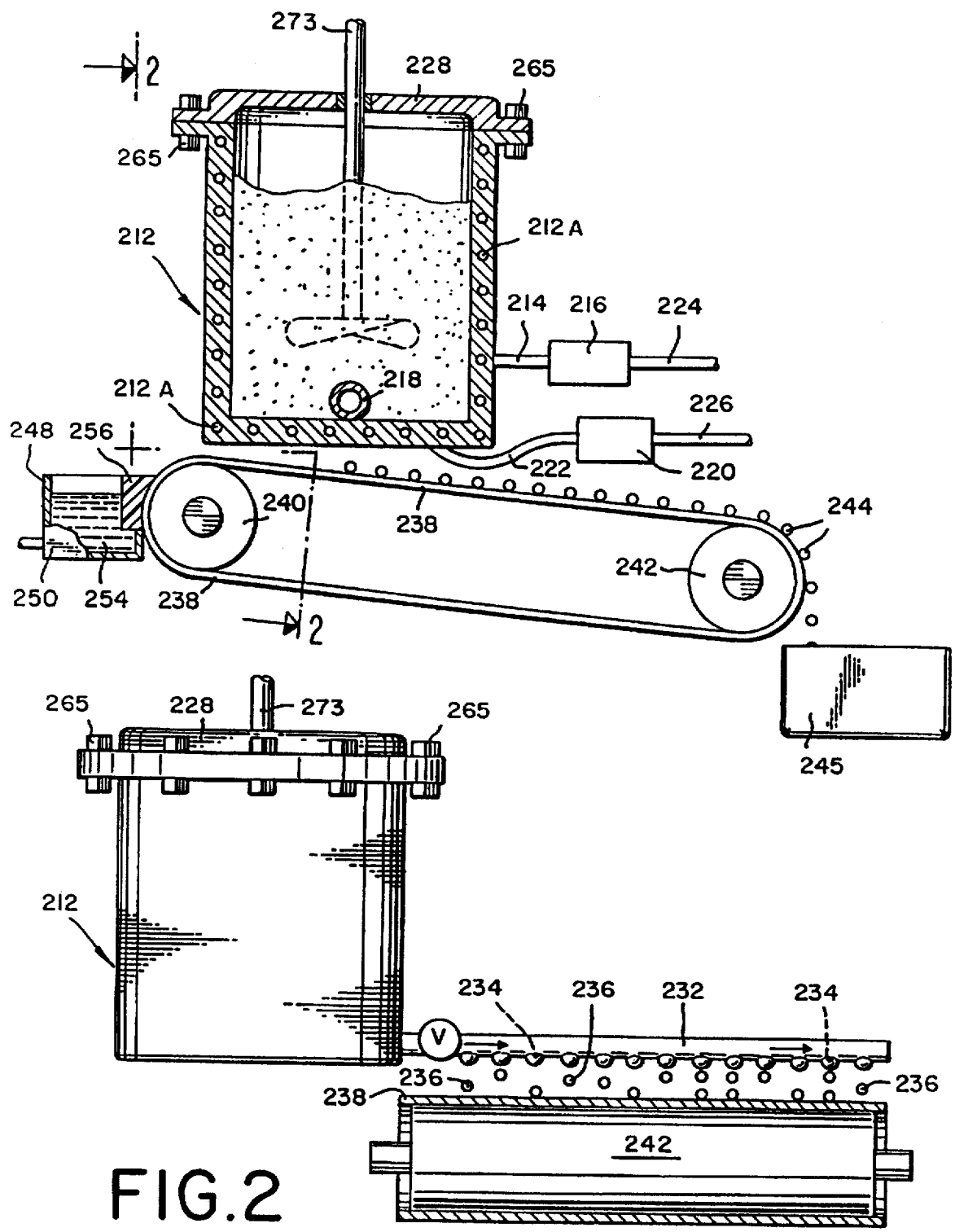
FIG. 1 is a partial side elevation and partial sectional view of an apparatus for forming polymer pellets containing the 1(3H)-isobenzofuranone of our invention.
FIG. 2 is a section taken along line 2—2 of FIG. 1.

Referring to FIGS. 1 and 2, in particular, the apparatus used in producing polymeric fragrances containing the 1(3H)-isobenzofuranone of our invention comprises a device for forming scented polyolefin (for example) pellets, which comprises a vat or container 212 into which a mixture of polyolefins such as polyethylene and an aromatic substance or scented material is placed (in this case the 1(3H)-isobenzofuranone of our invention). The container is closed by an airtight lid 228 and clamped to the container by bolts 265. A stirrer 273 traverses the lid or cover 228 in an airtight manner and is rotated in a suitable manner. A surrounding cylinder 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with viscosity ranging between 180 and 220 Saybolt seconds and having a melting point in the range of 200°–280° F. The heating coils 212A are operated to maintain the upper portion of the container 212 within a temperature range of from 250°–350° F. The bottom portion of the container is heated by means of heating coils 212A heated through a control 220 connected thereto through a connecting wire 222 to maintain the lower portion of the container within a temperature range of from 250°–350° F.

Thus, polymer (e.g., polyethylene or polyvinyl alcohol) is added to container 212 and is heated from 10–12 hours whereafter a scented aroma imparting material (the 1(3H)-isobenzofuranone of our invention) is added quickly to the melt. The material must be compatible with the polyolefin or polyvinyl alcohol and forms a homogeneous liquid melt therewith. The scented material is of a type for the particular aroma desired and formulated specifically for the scenting purpose for which the polyolefin or polyvinyl alcohol will be employed.

Generally about 5–30% by weight of the scented material (containing the 1(3H)-isobenzofuranone of our invention) are added to the polyolefin or polyvinyl alcohol.

After the scent imparting material (e.g., a composition containing the 1(3H)-isobenzofuranone of our invention) is added to the container 212; the mixture is stirred for a few minutes, for example, 5–15 minutes and maintained within the temperature range as indicated previously by heating coils 212A. The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter, the valve "V" is opened permitting the mass to flow outwardly through the conduit 218/232 having a multiplicity of orifices 234 adjacent to the lower side thereof. The outer end of the conduit 218/232 is closed so that the liquid polymer (e.g., polyolefin or polyvinyl alcohol) and aroma imparting material (e.g., the 1(3H)-isobenzofuranone of our invention) will continuously drop through orifices 234 downwardly from conduit 232. During this time, the temperature of the polymer (e.g., polyethylene, polypropylene or polyvinyl alcohol) and scent imparting material (the 1(3H)-isobenzofuranone of our invention) is accurately controlled so that a temperature in the range of from about 210°14 275° F. will exist in the conduit 218/232. The regulation of the temperature through the controls 216 and 220 is essential in order to insure temperature balance to provide for the continuous dropping or dripping of molten polymer (e.g., polyethylene or polyvinyl alcohol) and scenting material (e.g., the 1(3H)-isobenzofuranone of our invention or a mixture of 1(3H)-isobenzofuranone with other perfume ingredients) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 245 and utilized in processes as illustrated, infra.

A feature of this aspect of the process of our invention is the provision for moistening of the conveyor belt 238 to insure rapid formation of the solid polymeric (e.g., polyolefin or polyvinyl alcohol) scented pellets 244 without sticking to material which will not normally stick to a melted plastic. A moistening means 248 insures a sufficiently cold temperature of the belt surface for adequate formation of the pellets 244. The adequate moistening means comprises a container 250 which is continuously fed with water 254 to maintain a level for moistening a sponge element 256 which bears against the exterior of the belt 238.

The following Examples I, et seq., serve to illustrate our invention and this invention is considered to be restricted thereto only as indicated in the appended claims.

All parts and percentages given herein are by weight unless otherwise specified.

EXAMPLE I

ROSE PERFUME

A rose perfume is prepared containing the following mixture:

| Ingredients | Parts by Weight |
| --- | --- |
| Rhodinol | 250 |
| β-Phenylethyl alcohol | 195 |
| α-methyl ionone | 80 |
| Linalyl acetate | 60 |
| Cis-3-hexenyl acetate | 5 |
| Jasmine absolute | 10 |
| Cinnamic alcohol | 20 |
| Rhodinyl acetate | 60 |
| Cyclohexyl ethyl alcohol | 20 |
| Geraniol (99%) | 130 |
| Geranyl acetate (99%) | 80 |
| Paraisopropyl cyclohexanol | 60 |
| Diethyl phthalate | 30 |
| Trans,trans-Δ-damascone | 30 |

| Ingredients | Parts by Weight |
| --- | --- |
| Compound having the structure: 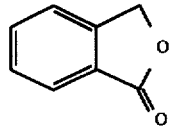 | 30 |

The 1(3H)-isobenzofuranone having the structure:

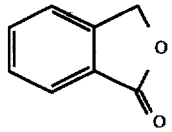

imparts to this rose formulation sweet, coumarin-like undertones and sweet, hay, heliotropin-like and almond-like topnotes. Accordingly, the formulation of Example I can be described as having "a rosy aroma with sweet and coumarin-like undertones and with sweet, hay, heliotropin-like and almond-like topnotes".

EXAMPLE II

PREPARATION OF COSMETIC POWDER COMPOSITIONS

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

| Substance | Aroma Description |
| --- | --- |
| The 1(3H)-isobenzofuranone having the structure: | A sweet, coumarin-like aroma with sweet, hay, heliotropin-like and almond-like topnotes. |
| Perfume composition of Example I. | A rosy aroma with sweet and coumarin-like undertones and with sweet, hay, heliotropin-like and almond-like topnotes. |

EXAMPLE III

PERFUMED LIQUID DETERGENTS

Concentrated liquid detergents (lysine salt of n-dodecylbenzene sulfonic acid as more specifically described in U.S. Pat. No. 3,948,818 issued on Apr. 6, 1976, incorporated by reference herein) with aroma nuances as set forth in Table I of Example II, are prepared containing 0.10%, 0.15%, 0.20%, 0.25%, 0.30% and 0.35% of the substance set forth in Table I of Example II. They are prepared by adding and homogeneously mixing the appropriate quantity of substance set forth in Table I of Example II in the liquid detergent. The detergents all possess excellent aromas as set forth in Table I of Example II, the intensity increasing with greater concentrations of substance as set forth in Table I of Example II.

EXAMPLE IV

PREPARATION OF COLOGNES AND HANDKERCHIEF PERFUMES

Compositions as set forth in Table I of Example II are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definite fragrances as set forth in Table I of Example II are imparted to the colognes and to the handkerchief perfumes at all levels indicated.

EXAMPLE V

PREPARATION OF SOAP COMPOSITIONS

100 Grams of soap chips (per sample) (IVORY® produced by the Procter & Gamble Company of Cincinnati, Ohio) are each mixed with one gram of samples of substances as set forth in Table I of Example II until homogeneous compositions are obtained. In each of the cases, the homogeneous compositions are heated under 8 atmospheres pressure at 180° C. for a period of 3 hours and the resulting liquids are placed into soap molds. The resulting soap cakes, on cooling, manifest aromas as set forth in Table I of Example II.

EXAMPLE VI

PREPARATION OF SOLID DETERGENT COMPOSITIONS

Detergents are prepared using the following ingredients according to Example I of Canadian Patent No. 1,007,948 (incorporated by reference herein):

| Ingredient | Percent by Weight |
| --- | --- |
| NEODOL ® 45-11 (a $C_{14}$–$C_{15}$ alcohol ethoxyated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example II. Each of the detergent samples has an excellent aroma as indicated in Table I of Example II.

EXAMPLE VII

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and the perfuming material are as follows:

a water "dissolvable" paper ("Dissolvo Paper");

ADOGEN® 448 (m.p. about 140° F.) as the substrate coating; and an outer coating having the following formulation (m.p. about 150° F.):

57% $C_{20-22}$HAPS;

22% isopropyl alcohol;

20% antistatic agent; and

1% of one of the substances as set forth in Table I of Example II.

Fabric softening compositions prepared according to Example I at column 15 of U.S. Pat. No. 3,632,396 having aroma characteristics as set forth in Table I of Example II, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example II is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table I of Example II, supra.

EXAMPLE VIII

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| | |
| --- | --- |
| Dioctyl sebacate | 0.05 weight percent |
| Benzyl alcohol | 0.10 weight percent |
| Dow Corning 473 fluid (prepared by the Dow Corning Corporation) | 0.10 weight percent |
| TWEEN ® 20 surfactant (prepared by ICI America Corporation) | 0.03 weight percent |
| One of the perfumery substances as set forth in Table I of Example II. | 0.10 weight percent |

The perfuming substances as set forth in Table I of Example II add aroma characteristics as set forth in Table I of Example II which are rather intense and aesthetically pleasing to the users of the soft-feel, good-hold pump hair sprays.

EXAMPLE IX

CONDITIONING SHAMPOOS

Monamid CMA (prepared by the Mona Industries Company) (3.0 weight percent) is melted with 2.0 weight percent coconut fatty acid (prepared by the Procter & Gamble Company of Cincinnati, Ohio); 2.0 weight percent ethylene glycol distearate (prepared by the Armak Corporation) and triethanolamine (a product of the Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

GAFQUAT® 755N polymer (manufactured by the GAF Corporation of 140 West 51st Street, New York, N.Y.) (5.0 weight percent) is admixed with 0.1 weight percent sodium sulfite and 1.4 weight percent polyethylene glycol 6000 distearate produced by the Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table I of Example II is added to the mixture. The resulting mixture is cooled to 40° C. and blending is carried out for an additional one hour in each case. At the end of this blending period, the resulting material has a pleasant fragrance as indicated in Table I of Example II.

EXAMPLE X

Scented polyethylene pellets having a pronounced scent as set forth in Table I of Example II are prepared as follows:

75 Pounds of polyethylene of a melting point of about 220° F. are heated to about 230° F. in a container of the kind illustrated in FIGS. 1 and 2. 25 Pounds of each of the perfume materials of Table I of Example II, supra, are then added quickly to the liquified polyethylene. The lid 228 is put in place and the agitating means 273 are actuated. The temperature is maintained at about 225° F. and the mixing is then continued for about 5–15 minutes. The valve "V" is then opened to allow flow of the molten polyethylene enriched with each of the aroma substance-containing materials to exit through the orifices 234. The liquid falling through the orifices 234 solidify almost instantaneously upon impact with the moving, cooled conveyor 238. Solid polyethylene beads or pellets 244 having pronounced aromas as set forth in Table I of Example II, supra, are then formed. Analysis demonstrates that the pellets contain about 25% of each of the perfume substances of Table I of Example II so that almost no losses of the scenting substance occur. These pellets may be called master pellets.

50 Pounds of the scent-containing master pellets are then added to 1,000 pounds of unscented polyethylene powder and the mass is heated to the liquid state. The liquid is molded into thin sheets or films. The sheets or films have a pronounced aroma as set forth in Table I of Example II, supra. The sheets are also fabricated into garbage bags which have aromas as set forth in Table I of Example II, supra.

What is claimed is:

1. A cologne consisting essentially of water, ethanol and an aroma imparting quantity of the 1(3H)-isobenzofuranone having the structure:

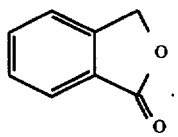

2. A process for augmenting or enhancing the aroma of a consumable material selected from the group consisting of perfume compositions, perfumed articles and colognes comprising the step of intimately admixing with a perfume base, perfumed article base or a cologne base an aroma augmenting, enhancing or imparting quantity of the 1(3H)-isobenzofuranone having the structure:

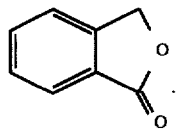

* * * * *